United States Patent [19]
Hoffmann et al.

[11] 3,974,171
[45] Aug. 10, 1976

[54] O-[3-METHYL-1,3,4-TRIAZOLE-(2,3,-b)-THIAZOL(6)YL]-(THIONO)-PHOSPHORIC(PHOSPHONIC) ACID ESTERS

[75] Inventors: Hellmut Hoffmann, Wuppertal; Ingeborg Hammann, Cologne; Wolfgang Behrenz, Overath-Steinenbrueck; Wilhelm Stendel, Wuppertal, all of Germany

[73] Assignee: Bayer Aktiengesellschaft, Leverkusen, Germany

[22] Filed: Oct. 7, 1974

[21] Appl. No.: 512,632

[30] Foreign Application Priority Data
Oct. 9, 1973 Germany............................ 2350631

[52] U.S. Cl.................. 260/306.7 E; 260/306.7 T; 260/308 C; 260/481 C; 424/200
[51] Int. Cl.².......................................... C07D 249/00
[58] Field of Search ............................ 260/306.7 E

[56] References Cited
UNITED STATES PATENTS

| | | | |
|---|---|---|---|
| 3,496,178 | 2/1970 | Scherer et al. ................ | 260/256.4 E |
| 3,681,352 | 8/1972 | Rosenfeld et al. ............ | 260/256.4 E |
| 3,682,943 | 8/1972 | Hoffmann et al. ............ | 260/306.7 E |

*Primary Examiner*—Raymond V. Rush
*Attorney, Agent, or Firm*—Burgess, Dinklage & Sprung

[57] ABSTRACT

O-[3-methyl-1,2,4-triazole-(2,3-b)-thiazol(6)yl]-(thiono)-phosphoric(phosphonic) acid esters of the formula

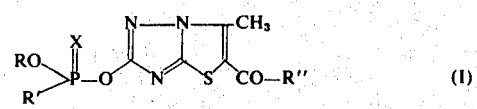

in which
R is alkyl with 1 to 6 carbon atoms,
R' is alkyl with 1 to 4 carbon atoms, alkoxy with 1 to 6 carbon atoms or phenyl,
R'' is amino, monoalkylamino or dialkylamino with 1 to 4 carbon atoms in each alkyl moiety or alkoxy with 1 to 6 carbon atoms, and
X is oxygen or sulfur,
which possess insecticidal and acaricidal properties.

7 Claims, No Drawings

O-[3-METHYL-1,3,4-TRIAZOLE-(2,3,-B)-THIAZOL(6)YL]-(THIONO)-PHOSPHORIC(PHOSPHONIC) ACID ESTERS

The present invention relates to and has for its objects the provision of particular new 0-[3-methyl-1,2,4-triazole-(2,3-b)-thiazol(6)yl]-(thiono)-phosphoric(-phosphonic) acid esters, i.e. 0,0-dialkyl-0-[2-carboalkoxy- or -carbamido-3-methyl-1,2,4-triazole-(2,3-b)-thiazol(6)yl]-phosphoric acid esters, their thiono counterparts, and their alkanephosphonic acid ester counterparts, which possess insecticidal or acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It has been disclosed in U.S. Pat. No. 2,754,244 that pyrazolothionophosphoric acid esters, such as 0,0-diethyl-0-[3-methyl-pyrazolyl-(5)]-thionophosphoric acid ester (Compound A), have insecticidal and acaricidal activity.

The present invention provides, as new compounds, the triazolothiazole-(thiono)-phosphoric(phosphonic) acid esters of the general formula

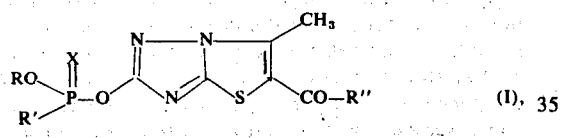

in which
R is alkyl with 1 to 6 carbon atoms,
R' is alkyl with 1 to 4 carbon atoms, alkoxy with 1 to 6 carbon atoms or phenyl,
R'' is amino, monoalkylamino or dialkylamino with 1 to 4 carbon atoms in each alkyl moiety or alkoxy with 1 to 6 carbon atoms, and
X is oxygen or sulfur.

Preferably R is straight-chain or branched alkyl with 1 to 3 carbon atoms; R' is straight-chain or branched alkyl with 1 to 3 carbon atoms, alkoxy with 1 to 3 carbon atoms or phenyl; and R'' is amino, monoalkylamino or dialkylamino with 1 to 3 carbon atoms in each alkyl moiety or alkoxy with 1 to 4 carbon atoms.

Surprisingly, the triazolo-thiazole(thiono)-phosphoric (phosphonic) acid esters according to the invention have a substantially better insecticidal and acaricidal action than prior-art compounds of analogous structure and of the same type of action. The compounds according to the invention thus represent a genuine enrichment of the art.

The present invention also provides a process for the preparation of a triazolothiazole-(thiono)-phosphoric(-phosphonic) acid ester of the formula (I), in which a (thiono)phosphoric(phosphonic) acid ester halide of the general formula

in which
X, R and R' have the above-mentioned meanings and Hal is hydrogen, is reacted with a triazolothiazole derivative of the general formula

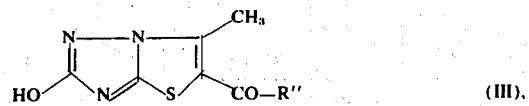

in which
R'' has the above-mentioned meaning, the latter being employed in the presence of an acid-binding agent or in the form of a salt.

If, for example, 2-carbethoxy-3-methyl-6-hydroxy-1,2,4-triazole-(2,3-b)-thiazole and 0-ethylthionophenylphosphonic acid ester chloride are used as starting compounds, the course of the reaction can be represented by the following equation:

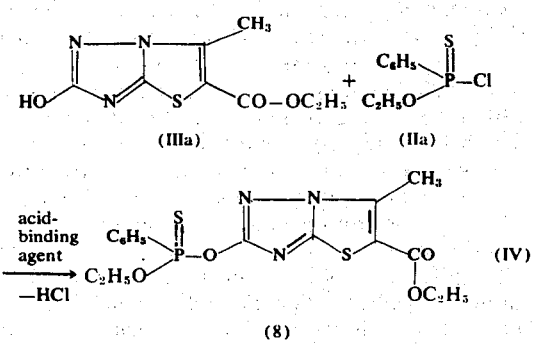

The (thiono)phosphoric(phosphonic) acid ester halides (II) to be used as starting compounds are already described in the literature and are obtainable according to customary processes, e.g. U.S. Pat. No. 3,167,574 and German Published Specification DAS 1,067,017.

The following may be mentioned as examples thereof: O,O-dimethyl-, O,O-diethyl-, O,O-di-n-propyl, O,O-diisopropyl-, O-ethyl-O-n-propyl, O-ethyl-O-isopropyl- and O-n-propyl-O-methyl-phosphoric acid ester chloride and the corresponding thiono analogues, and also O-methyl-, O-ethyl-, O-n-propyl- and O-isopropyl-methane-, or -ethane- or -propane- or -phenyl-phosphonic acid ester chloride and the corresponding thiono analogues.

The triazolothiazole derivatives (III) which are also required as starting materials are, in some cases, new, but can be prepared according to processes which are known in principle, by reacting, for example, thiosemicarbazide with pyrocarbonic acid ethyl ester to give the intermediate product of the formula $$H_2N-CS-NH-NH-CO-CO_2H_5 \qquad (V),$$

then cyclizing this in the presence of alkali metal alcoholate and subsequently reacting the product with, for example, chloroacetoacetic acid alkyl esters and then closing the thiazole ring in the presence of mineral acids, for example sulfuric acid, in accordance with the following equation:

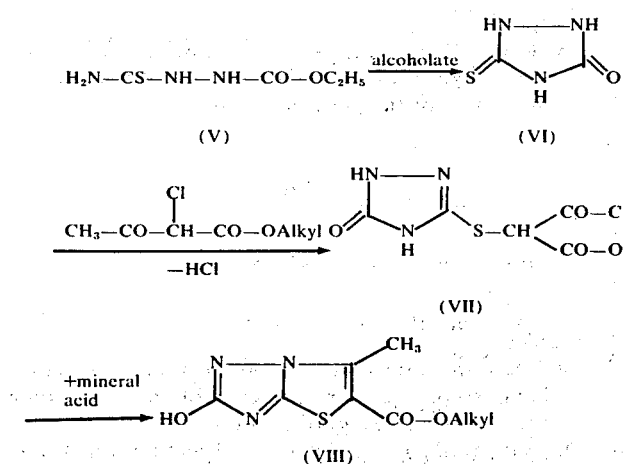

The triazolothiazole derivatives (VIII) thus obtained can optionally be converted to the corresponding carbaminyl compounds by means of ammonia or primary or secondary amines.

The following may be mentioned as examples of triazolothiazole derivatives (III) to be reacted in accordance with the process: 2-carbomethoxy-, 2-carboethoxy-, 2-carbo-n-propoxy-, 2-carbo-isopropoxy-, 2-carbo-butoxy-, 2-carbaminyl-, 2-N-methyl- and N,N-dimethyl-, N-ethyl-, N,N-diethyl-, N-n-propyl-, N,N-di-n-propyl-, N-isopropyl- and N,N-di-isopropylcarbaminyl-3-methyl-6-hydroxy-triazolo-(1,2,4)-thiazoles.

The process of preparation is preferably carried out with the use of suitable solvents and diluents. Practically all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

As mentioned above, the reaction may be conducted in the presence of an acid-binding agent. All customary acidbinding agents can be used for this purpose. Alkali metal carbonates and alkali metal alcoholates, such as sodium carbonate, potassium carbonate, sodium methylate, potassium methylate, sodium ethylate and potassium ethylate, have proved particularly suitable, as have aliphatic, aromatic or heterocyclic amines, for example triethylamine, dimethylamine, dimethylaniline, dimethylbenzylamine and pyridine.

Instead of working in the presence of acid-binding agents, it is equally possible first to prepare a salt, preferably an alkali metal salt or ammonium salt, of the hydroxy-triazolothiazole derivative (III), and then to react the salt with the ester halide (II).

The reaction temperature can be varied within a fairly wide range. In general, the reaction is carried out at between 0° and 120°C and preferably at from 70° to 90°C. The reaction is generally carried out under normal pressure.

To carry out the process, preferably equimolar amounts of the reactants are employed at the stated temperatures, in the presence of an acid acceptor if required and of one of the above-mentioned solvents. The reaction is complete after stirring the mixture at elevated temperature for one or more hours. The reaction mixture is poured into water and extracted by shaking with an organic solvent, for example benzene, and the organic phase is separated off. The latter is washed and dried, the solvent is stripped off under reduced pressure, and the residue is subjected to "slight distillation" and at times solidifies to crystals.

The compounds according to the invention are in a number of cases obtained in the form of oils which frequently cannot be distilled without decomposition but can be freed from the last volatile constituents by so-called "slight distillation," that is to say prolonged heating under reduced pressure to moderately elevated temperatures, and can be purified in this way. They are characterized by their refractive indexes. Those compounds that are obtained in crystalline form may be characterized by their melting points.

As has already been mentioned, the triazolothiazole(thiono)-phosphoric(phosphonic) acid esters according to the invention are distinguished by an outstanding insecticidal and acaricidal activity. The new products can not only be employed against insects and mites which damage plants, but also against pests harmful to health and pests of stored products in the veterinary field against animal ectoparasites, such as, for example, parasitic fly larvae. They couple a low phytotoxicity with a good action against both sucking and biting insects and against mites (Acarina).

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus heterae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly caterpillars (*Lepidoptera*) such as the diamond-back moth (*Plutella maculipennis*), the gypsy moth (*Lymantria dispar*), the browntail moth (*Euproctis chrysorrhoea*) and tent caterpillar (*Malacosoma neustria*); further, the cabbage moth (*Mamestra brassicae*) and the cut-worm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuhniella*) and greater wax moth (*Galleria mellonella*).

Also to be classed with the biting insects are beetles (*Coleoptera*), for example the granary weevil (*Sitophilus granarius = Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius = Acanthoscelides obtectus*), the leather beetle (*Dermestes frischi*), the khapra beetle (*Trogoderma granarium*), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes* spec.) and larvae of the cockchafer (*Melolontha melolontha*); cockroaches, such as the German cockroach (*Blattella germanica*), American cockroach (*Periplaneta americana*), Madeira cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, *Orthoptera*, for example the house cricket (*Gryllus domesticus*); termites such as the eastern subterranean termite (*Reticulitermes flavipes*) and *Hymenoptera* such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and blue-bottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (Acarina) there are classed, in particular, the spider mites (Tetranychidae) such as the two-spotted spider mite (*Tetranychus urticae*) and the European red mite (*Paratetranychus pilosus = Panonychus ulmi*), gall mites, for example the blackcurrant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against pests harmful to health and pests of stored products, particularly flies and mosquitoes, the present components are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides, or rodenticides, fungicides, bactericides, nematocides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Phaedon larvae test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) were sprayed with the preparation of the active compound until dripping wet and were then infested with mustard beetle larvae (*Phaedon cochleariae*).

After the specified periods of time, the degree of destruction was determined in %: 100% means that all beetle larvae were killed, whereas 0% means that none of the beetle larvae were killed.

The active compounds, the concentrations of the active compounds, the evaluation times and the results can be seen from the following table:

Table 1

(*Phaedon* larvae test)

| Active compound | Active compound concentration in % | Degree of destruction in % after 3 days |
|---|---|---|
| $(C_2H_5O)_2\overset{S}{\overset{\|}{P}}-O-\underset{H}{\underset{\|}{\diagdown N-N \diagup}}\diagup^{CH_3}$ (known) (A) | 0.1<br>0.01<br>0.001 | 100<br>100<br>0 |
| $(C_2H_5O)_2\overset{S}{\overset{\|}{P}}-O-\underset{N}{\underset{\diagdown}{\diagup}}\underset{S}{\underset{\diagup}{\diagdown}}\diagup^{N---N}\diagdown_{CO-OCH_3}^{CH_3}$ (1) | 0.1<br>0.01<br>0.001<br>0.0001 | 100<br>100<br>100<br>60 |
| $(C_2H_5O)_2\overset{S}{\overset{\|}{P}}-O-\underset{N}{\underset{\diagdown}{\diagup}}\underset{S}{\underset{\diagup}{\diagdown}}\diagup^{N---N}\diagdown_{CO-OC_2H_5}^{CH_3}$ (2) | 0.1<br>0.01<br>0.001 | 100<br>100<br>100 |
| $(C_2H_5O)_2\overset{S}{\overset{\|}{P}}-O-\underset{N}{\underset{\diagdown}{\diagup}}\underset{S}{\underset{\diagup}{\diagdown}}\diagup^{N---N}\diagdown_{CO-NH-CH_3}^{CH_3}$ (6) | 0.1<br>0.01<br>0.001 | 100<br>100<br>95 |

EXAMPLE 2

Plutella test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed whereas 0% means that none of the caterpillars were killed.

The active compounds, the concentrations of the active compounds, the evaluation times and the results can be seen from the following table:

EXAMPLE 3

Myzus test (contact action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which have been heavily infested with peach aphids (*Myzus persicae*) were sprayed with the preparation of the active compound until dripping wet.

After the specified periods of time, the degree of destruction was determined as a percentage: 100% means that all the aphids were killed, whereas 0% means that none of the aphids were killed.

The active compounds, the concentrations of the active compounds, the evaluation times and the results can be seen from the following table:

Table 2

| Active compound | (*Plutella* test) Active compound concentration in % | Degree of destruction in % after 3 days |
|---|---|---|
| $(C_2H_5O)_2P(=S)-O-$ [pyrazole ring with CH$_3$, NH] (known) (A) | 0.1<br>0.01<br>0.001 | 100<br>60<br>0 |
| $(CH_3O)_2P(=S)-O-$ [thiazolo-triazine ring with CH$_3$, CO—OCH$_3$] (3) | 0.1<br>0.01<br>0.001 | 100<br>100<br>80 |
| $(C_2H_5O)_2P(=S)-O-$ [thiazolo-triazine ring with CH$_3$, CO—OCH$_3$] (1) | 0.1<br>0.01<br>0.001<br>0.0001 | 100<br>100<br>100<br>100 |
| $C_2H_5O-P(=S)(C_2H_5)-O-$ [thiazolo-triazine ring with CH$_3$, CO—OCH$_3$] (4) | 0.1<br>0.01<br>0.001 | 100<br>100<br>40 |
| $(C_2H_5O)_2P(=S)-O-$ [thiazolo-triazine ring with CH$_3$, CO—OC$_2$H$_5$] (2) | 0.1<br>0.01<br>0.001 | 100<br>100<br>100 |

Table 3

| Active compound | (*Myzus* test) Active compound concentration in % | Degree of destruction in % after 1 day |
|---|---|---|
| $(C_2H_5O)_2P(=S)-O-$ [pyrazole ring with CH$_3$, NH] (known) (A) | 0.1<br>0.01<br>0.001 | 99<br>40<br>0 |

Table 3-continued

| Active compound | (Myzus test) Active compound concentration in % | Degree of destruction in % after 1 day |
|---|---|---|
| (CH₃O)₂P(S)—O—[imidazothiazole with CH₃ and CO—OCH₃] (3) | 0.1<br>0.01<br>0.001<br>0.0001 | 100<br>100<br>100<br>100 |
| (C₂H₅O)₂P(S)—O—[imidazothiazole with CH₃ and CO—OCH₃] (1) | 0.1<br>0.01<br>0.001<br>0.0001 | 100<br>100<br>100<br>60 |
| C₂H₅O(C₂H₅)P(S)—O—[imidazothiazole with CH₃ and CO—OCH₃] | 0.1<br>0.01<br>0.001<br>0.0001 | 100<br>100<br>99 |
| (C₂H₅O)₂P(S)—O—[imidazothiazole with CH₃ and CO—OC₂H₅] (2) | 0.1<br>0.01<br>0.001 | 100<br>100<br>75 |
| (C₂H₅O)₂P(S)—O—[imidazothiazole with CH₃ and CO—NH—CH₃] (6) | 0.1<br>0.01<br>0.001 | 100<br>100<br>40 |

EXAMPLE 4

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the two-spotted spider mite (*Tetranychus urticae*) in all stages of development.

After the specified periods of time, the effectiveness of the preparation of active compound was determined by counting the dead mites. The degree of destruction thus obtained is expressed as a percentage: 100% means that all the spider mites were killed, whereas 0% means that none of the spider mites were killed.

The active compounds, the concentrations of the active compounds, the evaluation times and the results can be seen from the following table:

Table 4

| Active compound | Tetranychus test (resistant) Active compound concentration in % | Degree of destruction in % after 2 days |
|---|---|---|
| (C₂H₅O)₂P(S)—O—[pyrazole with CH₃, N—H] (A) (known) | 0.1<br>0.01 | 50<br>0 |
| (C₂H₅O)₂P(S)—O—[imidazothiazole with CH₃ and CO—OC₂H₅] (2) | 0.1<br>0.01 | 90<br>40 |

EXAMPLE 5

LT$_{100}$ test for Diptera
Test insects: *Musca domestica*
Solvent: Acetone 2 parts by weight of active compound were dissolved in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test insects were then placed in the Petri dish and it was covered with a glass lid.

The condition of the test insects was continuously observed. The time which was necessary for 100% destruction was determined.

The test insects, the active compounds, the concentrations of the active compounds and the times at which there was 100% destruction can be seen from the following table:

EXAMPLE 6

LT$_{100}$ test for Diptera
Test insects: *Aedes aegypti*
Solvent: Acetone 2 parts by weight of active compound were dissolved in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test insects were then placed in the Petri dish and it was covered with a glass lid.

The condition of the test insects was continuously observed. The time which was necessary for 100% destruction was determined.

The test insects, the active compounds, the concentrations of the active compounds and the times at which there was 100% destruction can be seen from the following table:

Table 5

| Active compound | (LT$_{100}$ test for *Diptera* / *Musca domestica*) Active compound concentration in % | LT$_{100}$ in minutes (') or hours (h) |
|---|---|---|
| 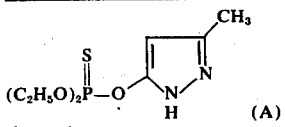 (known) | 0.2<br>0.02 | 105'<br>6h = 75% |
| 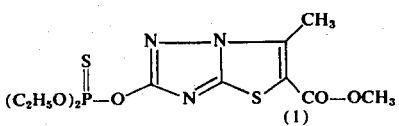 (1) | 0.2<br>0.02 | 80'<br>200' |
| 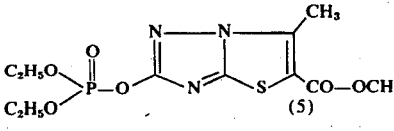 (5) | 0.2<br>0.02<br>0.002 | 55'<br>145'<br>6h = 90% |
| 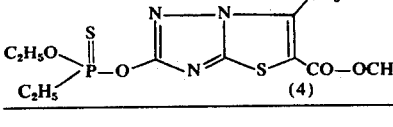 (4) | 0.2<br>0.02<br>0.002 | 90'<br>195'<br>6h |

Table 6

| Active compound | (LT$_{100}$ test for *Diptera* / *Aedes aegypti*) Active compound concentration of the solution in % | LT$_{100}$ in hours (h) |
|---|---|---|
| 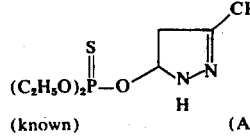 (known) (A) | 0.2 | 3h |
| 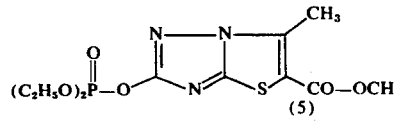 (5) | 0.2<br>0.02 | 1h<br>2h |

Table 6-continued (LT$_{100}$ test for *Diptera / Aedes aegypti*)

| Active compound | Active compound concentration of the solution in % | LT$_{100}$ in hours (h) |
|---|---|---|
| 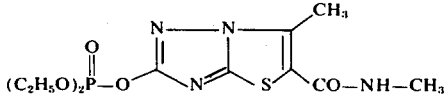 (7) | 0.2<br>0.02 | 1h<br>2h |
| 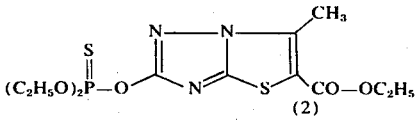 (2) | 0.2<br>0.02 | 1h<br>2h |

EXAMPLE 7

LD$_{100}$ test
Test insects: *Sitophilus granarius*
Solvent: Acetone 2 parts by weight of the active compound were dissolved in 1,000 parts by volume of the solvent. The solution so obtained was diluted with further solvent to the desired concentration.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per m$^2$ of filter paper varied with the concentration of the solution of active compound. About 25 test insects were then placed in the Petri dish and it was covered with a glass lid.

The condition of the test insects was observed 3 days after the commencement of the experiments. The destruction, in %, was determined.

The active compounds, the concentrations of the active compounds, the test insects and the results can be seen from the following table:

Table 7

(LD$_{100}$ test / *Sitophilus granarius*)

| Active compound | Active compound concentration of the solution in % | Degree of destruction in % |
|---|---|---|
| 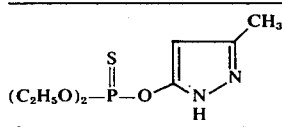 (known) (A) | 0.2<br>0.02 | 100<br>0 |
| 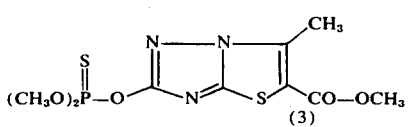 (3) | 0.2<br>0.02 | 100<br>100 |
| 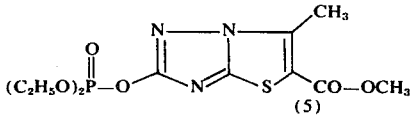 (5) | 0.2<br>0.02<br>0.002 | 100<br>100<br>50 |
| 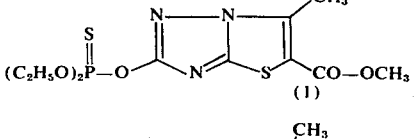 (1) | 0.2<br>0.02 | 100<br>100 |
| 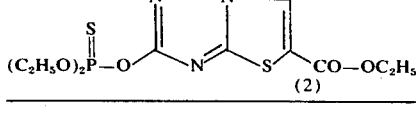 (2) | 0.2<br>0.02 | 100<br>100 |

EXAMPLE 8

Test with parasitic fly larvae
Solvent: 35 parts by weight of ethylene polyglycol monomethyl ether
Emulsifier: 35 parts by weight of nonylphenyl polyglycol ether To produce a suitable preparation of active compound, 30 parts by weight of the active substance in question were mixed with the stated amount of solvent which contained the above-mentioned proportion of nonylphenol polyglycol ether and the concentrate thus obtained was diluted with water to the desired concentration.

About 20 fly larvae (*Lucilia cuprina*) were introduced into a test tube which contained approximately 2 ml of horse muscle. 0.5 ml of the preparation of active compound was applied to this horse meat. After 24 hours, the degree of destruction in % was determined. 100% means that all larvae had been killed and 0% means that no larvae had been killed.

The active compounds tested, active compound concentrations used and results obtained can be seen from the table which follows:

filtered off and recrystallized from ethanol. 121 g (74% of theory) of the product of the above formula, of decomposition point 165° to 168°C, were obtained.

b.

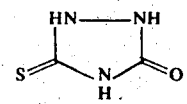

82 g (0.5 mole) of the product prepared as described under (a), in 300 ml of methanol, were treated with 0.5 mole of sodium methylate.

After heating for 5 hours under reflux, the mixture was cooled and evaporated, the residue was taken up in water and hydrochloric acid was added to the reaction mixture. The precipitate which had separated out was filtered off and dried on clay. 24 g (41% of theory) of the above product, of melting point 193°C (with decomposition) were obtained.

Table 8

| Active compound | (Test with parasitic fly larvae / *Lucilia cuprina*) Active compound concentration in ppm | Degree of destruction in % (*Lucilia cuprina* res.) |
|---|---|---|
| (C$_2$H$_5$O)$_2$P(S)—O—[N—N=C(CH$_3$)—S—C(CO—OCH$_3$)=N] (1) | 100<br>30<br>10<br>3 | 100<br>100<br>100<br>50 |
| (CH$_3$O)$_2$P(S)—O—[N—N=C(CH$_3$)—S—C(CO—OCH$_3$)=N] (3) | 100<br>10<br>1 | 100<br>100<br>100 |
| (C$_2$H$_5$O)$_2$P(O)—O—[N—N=C(CH$_3$)—S—C(CO—OCH$_3$)=N] (5) | 100<br>10 | 100<br>100 |

The process of the present invention is illustrated by the following preparative Examples.

EXAMPLE 9 a.

$$H_2N-CS-NH-NH-CO-OC_2H_5 \quad (V)$$

A mixture of 162 g of pyrocarbonic acid diethyl ester, 91 g of thiosemicarbazide and 300 ml of chloroform was boiled under reflux for 3 hours. After cooling the batch, the precipitate which had separated out was c.

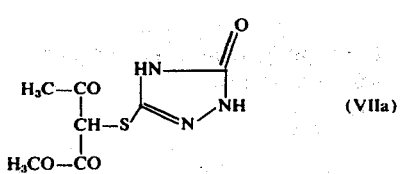

76 g of chloroacetoacetic acid methyl ester were added to a mixture of 70 g (0.5 mole) of the sodium salt of the product prepared under (b), in 400 ml of methanol, and the reaction mixture was stirred overnight. The precipitate was then filtered off and the filter cake was washed with water, dried and recrystallized from ethyl acetate. 68 g (59% of theory) of the above substance, of melting point 147°C, were obtained.

d.

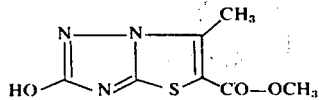 (VIIIa)

46 g (0.2 mole) of the substance obtained as described under (c) were added to 70 ml of sulfuric acid, in the course of which the temperature of the mixture rose to 60°C. The batch was stirred until the solid constituents had dissolved, and was left to stand overnight. The reaction mixture was then poured onto ice and the solution was buffered with sodium acetate. The residue was filtered off, washed with water and dried. 28 g (66% of theory) of 2-carbomethoxy-3-methyl-6-hydroxy-1,2,4-triazole-(2,3-b)-thiazole of melting point 204° to 206°C were obtained.

e. The following compound was prepared analogously:

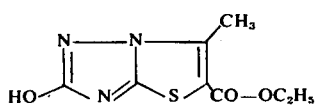

The melting point was about 216°–218°C and the yield was 51% of theory.

f.

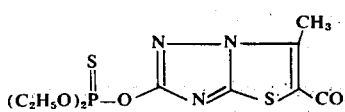 (1)

A mixture of 21 g (0.1 mole) of 2-carbomethoxy-3-methyl-6-hydroxy-1,2,4-triazole-(2,3-b)-thiazole produced in (d) hereinabove, 15 g of potassium carbonate and 19 g of O,O-diethylthionophosphoric acid ester chloride in 200 ml of acetonitrile was warmed to 80°C for 4 hours while stirring and was then poured into water. The mixture was extracted by shaking with benzene; after separation of the layers the organic phase was washed and dried, and the solvent was distilled off under reduced pressure. The residue was subjected to slight distillation and thereafter solidified to a crystalline mass. 26 g (71% of theory) of O,O-diethyl-O-[2-carbomethoxy-3-methyl-1,2,4-triazole-(2,3-b)-thiazol(6)yl]-thionophosphoric acid ester of melting point 74°C were obtained.

The following compounds were prepared by analogous methods:

| Compound No. | Structure | Physical properties (refractive index; melting point) | Yield (% of theory) |
|---|---|---|---|
| 2. | (C₂H₅O)₂P(S)—O—[triazolothiazole]—CO—OC₂H₅ | $n_D^{23}$: 1.5524 | 77 |
| 3. | (CH₃O)₂P(S)—O—[triazolothiazole]—CO—OCH₃ | 78°C | 51 |
| 4. | C₂H₅O(C₂H₅)P(S)—O—[triazolothiazole]—CO—OCH₃ | $n_D^{24}$: 1.5619 | 69 |
| 5 | (C₂H₅O)₂P(O)—O—[triazolothiazole]—CO—OCH₃ | 56°C | 63 |

EXAMPLE 10 a.

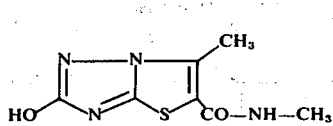

45 g (0.2 mole) of 2-carboethoxy-3-methyl-6-hydroxy-1,2,4-triazole-(2,3-b)-thiazole produced in Example 9 (d) were added to 200 ml of an aqueous 40 to 45% strength monomethylamine solution. The mixture was stirred for 2 hours at room temperature and the reaction mixture was then evaporated. The residue was dissolved in water and dilute hydrochloric acid was added to the solution. The precipitate which separated out was filtered off, dried on clay and recrystallized from methanol. 15 g (35% of theory) of 2-N-methylcarbamoyl-3-methyl-6-hydroxy-1,2,4-triazole-(2,3-b)-thiazole of melting point 250°C were obtained.

b.

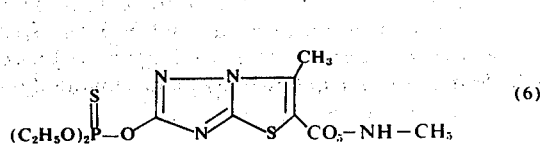 (6)

By the same process as in Example 9 (f) the product of (a) hereinabove was converted to O,O-diethyl-O-[2-N-methylcarbamoyl-3-methyl-1,2,4-triazole-(2,3-b)-thiazol(6)yl]-thionophosphoric acid ester in a yield of 57%, the product having a refractive index of $n_D^{26}$:1.5498.

EXAMPLE 11

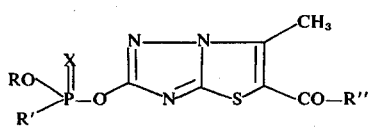 (7)

By the same process as in Example 10(b) except that the thionophosphoric acid ester chloride was replaced by O,O-diethylphosphoric acid ester chloride there was produced O,O-diethyl-O-[2-N-methylcarbamoyl-3-methyl-1,2,4-triazole-(2,3-b)-thiazol(6)yl]-phosphoric acid ester in a yield of 67%, the product having a melting point of 102°C.

It will be appreciated that the instant specification and examples are set forth by way of illustration and not limitation, and that various modifications and changes may be made without departing from the spirit and scope of the present invention.

What is claimed is:

1. An O-[3-methyl-1,3,4-triazole-(2,3-b)-thiazol(-6)yl]-(thiono)-phosphoric(phosphonic) acid ester of the formula

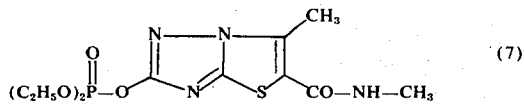 (I)

in which
R is alkyl with 1 to 6 carbon atoms,
R' is alkyl with 1 to 4 carbon atoms, alkoxy with 1 to 6 carbon atoms,
R'' is amino, monoalkylamino or dialkylamino with 1 to 4 carbon atoms in the or each alkyl moiety or alkoxy with 1 to 6 carbon atoms, and
X is oxygen or sulfur.

2. A compound according to claim 1, in which R is straight-chain or branched alkyl with 1 to 3 carbon atoms; R' is straight-chain or branched alkyl with 1 to 3 carbon atoms, alkoxy with 1 to 3 carbon atoms; and R'' is amino, monoalkylamino or dialkylamino with 1 to 3 carbon atoms in each alkyl moiety or alkoxy with 1 to 4 carbon atoms.

3. The compound acccording to claim 1 wherein such compound is O,O-diethyl-O-[2-carbomethoxy-3-methyl-1,2,4-triazole-(2,3-b)-thiazol(6)yl]-thionophosphoric acid ester of the formula

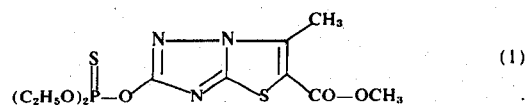 (1)

4. The compound according to claim 1 wherein such compound is O,O-diethyl-O-[2-carboethoxy-3-methyl-1,2,4-triazole-(2,3-b)-thiazol(6)yl]-thionophosphoric acid ester of the formula

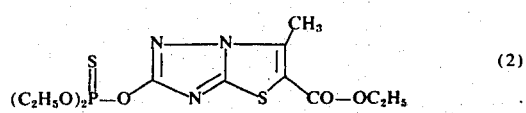 (2)

5. The compound according to claim 1 wherein such compound is O,O-dimethyl-O-[2-carbomethoxy-3-methyl-1,2,4-triazole-(2,3-b)-thiazol(6)yl]-thionophosphoric acid ester of the formula

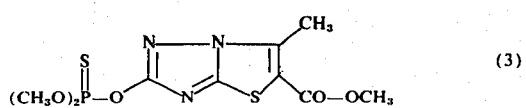 (3)

6. The compound according to claim 1 wherein such compound is O-ethyl-O-[2-carbomethoxy-3-methyl-1,2,4-triazole-(2,3-b)-thiazol(6)yl]-ethanethionophosphonic acid ester of the formula

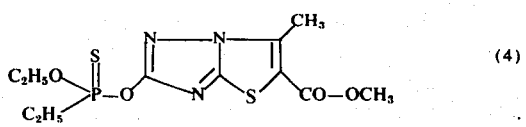 (4)

7. The compound according to claim 1 wherein such compound is O,O-diethyl-O-[2-N-methylcarbamoyl-3-methyl-1,2,4-triazole-(2,3-b)-thiazol(6)yl]-thionophosphoric acid ester of the formula

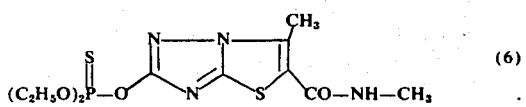 (6)

* * * * *